US005611349A

United States Patent [19]
Halleck et al.

[11] Patent Number: 5,611,349
[45] Date of Patent: Mar. 18, 1997

[54] RESPIRATION MONITOR WITH SIMPLIFIED BREATH DETECTOR

[75] Inventors: Michael E. Halleck, Longmont; Donald N. James, Estes Park, both of Colo.

[73] Assignee: I Am Fine, Inc., Bethesda, Md.

[21] Appl. No.: 439,505

[22] Filed: May 11, 1995

Related U.S. Application Data

[63] Continuation of Ser. No. 51,975, Apr. 26, 1993, abandoned.

[51] Int. Cl.⁶ ........................................................ A61B 5/08
[52] U.S. Cl. ............................................ 128/721; 128/782
[58] Field of Search .................................. 128/721, 722, 128/716, 671, 782; 310/331

[56] References Cited

U.S. PATENT DOCUMENTS

| | | |
|---|---|---|
| Re. 32,180 | 6/1986 | Lewiner et al. . |
| 2,184,511 | 12/1939 | Bagno et al. . |
| 3,268,845 | 8/1966 | Whitmore . |
| 3,290,521 | 12/1966 | Coleman et al. . |
| 3,572,316 | 3/1971 | Vogelman et al. . |
| 3,631,438 | 12/1971 | Lewin . |
| 3,782,368 | 1/1974 | Reibold . |
| 3,795,240 | 3/1974 | Frank . |
| 3,820,529 | 6/1974 | Gause et al. . |
| 3,882,847 | 5/1975 | Jacobs . |
| 3,940,974 | 3/1976 | Taylor . |
| 4,129,125 | 12/1978 | Lester et al. . |
| 4,308,870 | 1/1982 | Arkans . |
| 4,381,012 | 4/1983 | Russek . |
| 4,381,788 | 5/1983 | Douglas ............................ 128/722 |
| 4,576,179 | 3/1986 | Manua et al. . |
| 4,602,643 | 7/1986 | Dietz . |
| 4,732,159 | 3/1988 | Kramon ............................ 128/721 |
| 4,784,162 | 11/1988 | Ricks et al. . |
| 4,807,640 | 2/1989 | Watson et al. . |
| 4,813,428 | 3/1989 | Muraki et al. . |
| 4,889,131 | 12/1989 | Salem et al. . |
| 4,895,160 | 1/1990 | Reents . |
| 4,895,162 | 1/1990 | Dolliver . |
| 4,909,260 | 3/1990 | Salem et al. . |
| 5,022,402 | 6/1991 | Schieberl et al. . |
| 5,088,501 | 2/1992 | Niewisch . |
| 5,099,855 | 3/1992 | Yount . |
| 5,191,893 | 3/1993 | Reiten ............................... 128/721 |
| 5,277,194 | 1/1994 | Hosterman et al. . |
| 5,301,678 | 4/1994 | Watson et al. . |
| 5,329,932 | 7/1994 | Yount . |

FOREIGN PATENT DOCUMENTS

0019321  4/1980  European Pat. Off. .

*Primary Examiner*—Lee S. Cohen
*Attorney, Agent, or Firm*—Harold A. Burdick

[57] ABSTRACT

A respiration monitor is disclosed which includes a simplified pneumatic breath detector, a pressure sensor connected with the detector, and an active low pass filter for filtering the output of the monitor to reduce signals not indicative of respiration, such as movement of and/or impacts upon the detector. The monitor may be linked with a transmitter for remote subject monitoring, and the entire monitor may be configured to be unobtrusively worn by the subject.

18 Claims, 7 Drawing Sheets

RESPIRATION MONITOR WITH SIMPLIFIED BREATH DETECTOR

This is a continuation of application Ser. No. 08/051,975, filed Apr. 26, 1993, now abandoned.

FIELD OF THE INVENTION

This invention relates to physiological monitors, and, more particularly, relates to respiration monitors and breath detectors.

BACKGROUND OF THE INVENTION

Various respiration detecting and/or monitoring devices have been heretofore suggested and/or utilized in a variety of settings, and have included devices utilizing impedance plethysmography, inductance plethysmography, aural monitoring, EMG or EKG monitoring, strain gauges or the like. These devices all have different limitations, including undue complexity for some uses, inability to monitor, or distinguish between, different types of respiratory and/or unrelated events such as upper airway obstructions, breath holding, sighing, yawning and artifact both of a mechanical and electromagnetic nature.

In particular, a number of respiration detectors based on pneumatic principals have been heretofore suggested and/or utilized (see, for example, U.S. Pat. Nos. 4,602,643, 4,813, 428 and 5,022,402), such detectors also suffering from some of the same limitations, particularly those related to distinguishing between events sensed. Further improvement could thus still be utilized.

SUMMARY OF THE INVENTION

This invention provides a respiration monitor which includes a simplified, low cost breath detector, the monitor being reliable, capable of improved monitoring of and distinguishing between respiratory events, having a good signal to noise ratio, and being capable of significant artifact filtration.

The breath detector includes a flexible yet resilient hollow tube, preferably of one-piece construction, and having a fluid channel defined by a wall, the detector being configured so that only a single outlet for the channel is provided for connection with a transducer.

The tube, having a small diameter, is self supporting along most of its length for securement, either totally or partially, around a subject's torso, and is configured and made of material to provide a flexibility sufficient to respond, by deformation of the normal channel configuration, to breathing of a subject when thus secured but insufficient to totally close the channel when the wall is exposed to a variety of external pressures. The configuration of the tube also assures resiliency sufficient to regain shape of the normal channel configuration without other structural aid.

The overall monitor includes the respiration detector having a pressure sensor connected with the outlet thereof, the sensor having as an output an electrical signal which is variable with sensed pressure. A low pass filter is coupled with the sensor circuitry for receiving the signal from the sensor and reducing artifact in the signal not related to respiration of the subject thus providing an output therefrom indicative of the subject's respiration.

The low pass filter is preferably an active low pass filter and is configured to provide an output therefrom in phase with the signal received from the sensor and has a cutoff between about 2.0 and 2.5 Hz. The pressure sensor is preferably an electret pressure transducer, with the combination of the tube/detector therewith requiring no special housing or modification of the transducer.

Means for applying the breath detector adjacent to the subject's torso is provided, the sensor and related circuitry, the low pass filter, and a transmitter being mounted thereon.

It is therefore an object of this invention to provide an improved respiration monitor.

It is another object of this invention to provide a simplified breath detector structure.

It is still another object of this invention to provide a respiration monitor which includes a simplified, low cost breath detector, the monitor being reliable, capable of improved monitoring of and distinguishing between respiratory events, having a good signal to noise ratio, and being capable of significant artifact filtration.

It is still another object of this invention to provide a breath detector for connection with monitoring means for monitoring changes in capacity of the detector, the detector including a flexible yet resilient hollow tube of one-piece construction and having a fluid channel defined by a wall, the detector being configured so that only a single outlet for the channel is provided for connection with the monitoring means.

It is yet another object of this invention to provide a breath detector including a length of tube having a selected geometry, wherein the tube has a flexibility sufficient to respond, by deformation of its normal configuration, to breathing of a subject when secured adjacent to the subject's torso but insufficient to totally close the channel when the tube is exposed to a variety of external pressures, and wherein the tube has a resiliency sufficient to regain its shape after deformation without other structural aid.

It is still another object of this invention to provide a respiration monitor which includes a respiration detector defining a conduit for containing a quantity of fluid and having an outlet, a pressure sensor connected with the outlet of the detector and having as an output therefrom an electrical signal which is variable with sensed pressure, and a low pass filter for receiving the signal from the sensor and reducing artifact in the signal not related to respiration of a subject.

It is yet another object of this invention to provide a respiration monitor that includes structure for applying a breath detector adjacent to a subject's torso, the structure having a sensor, low pass filter and transmitter arrangement connected with the detector and mounted thereto.

It is still another object of this invention to provide a respiration monitor having an active low pass respiration signal filter configured to provide an output therefrom in phase with the respiration signal received thereby and having a cutoff between about 2.0 and 2.5 Hz.

It is yet another object of this invention to provide a respiration monitor having an electret pressure transducer connected with a pneumatic breath detector, the transducer being directly exposed to pressure changes exerted by the breath detector.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figures 1A, 1B:
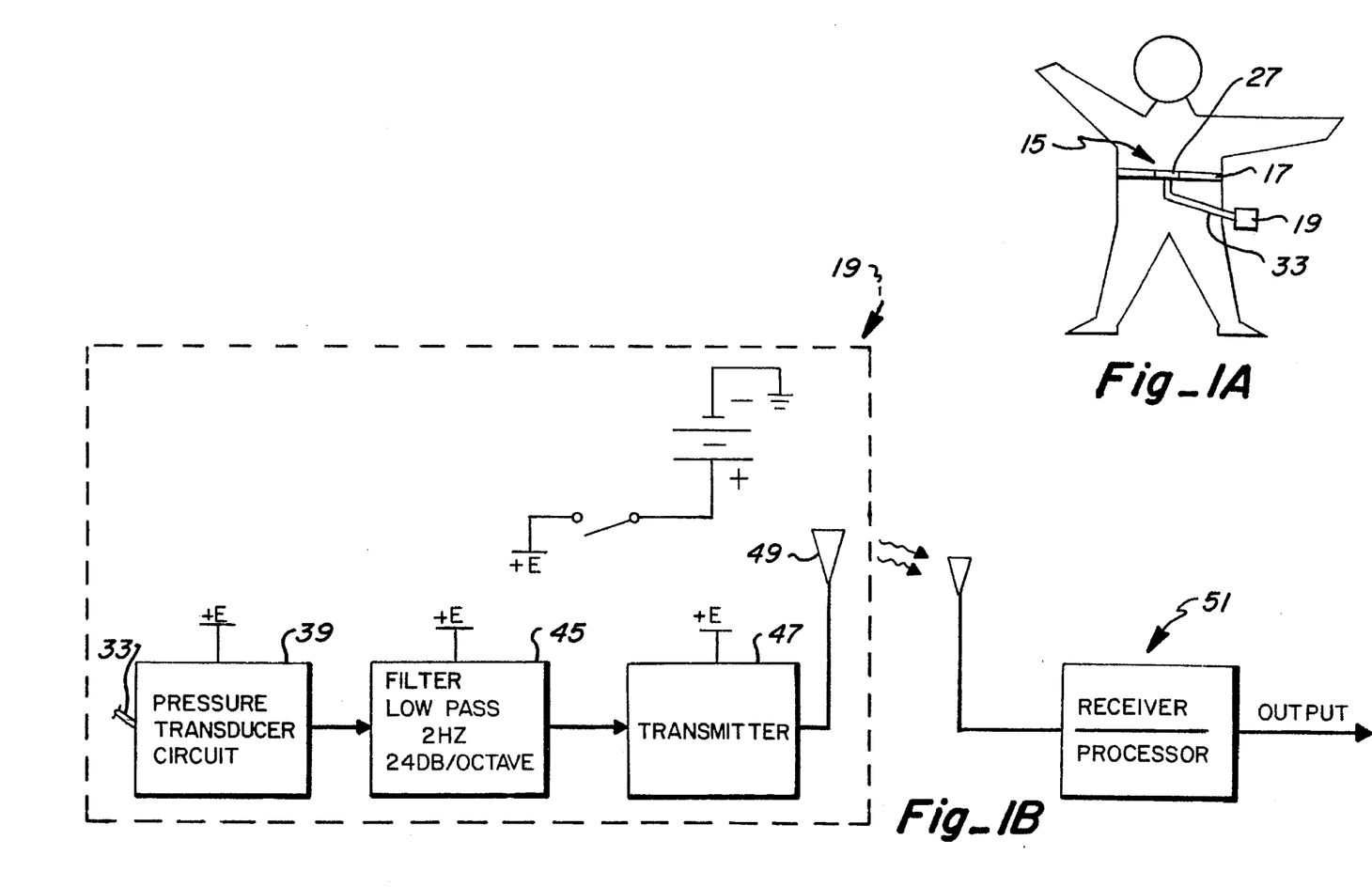
FIGS. 1A and 1B are schematic illustrations of the respiration monitor, including the breath detector, of this invention.
Figures 5, 6, 7:
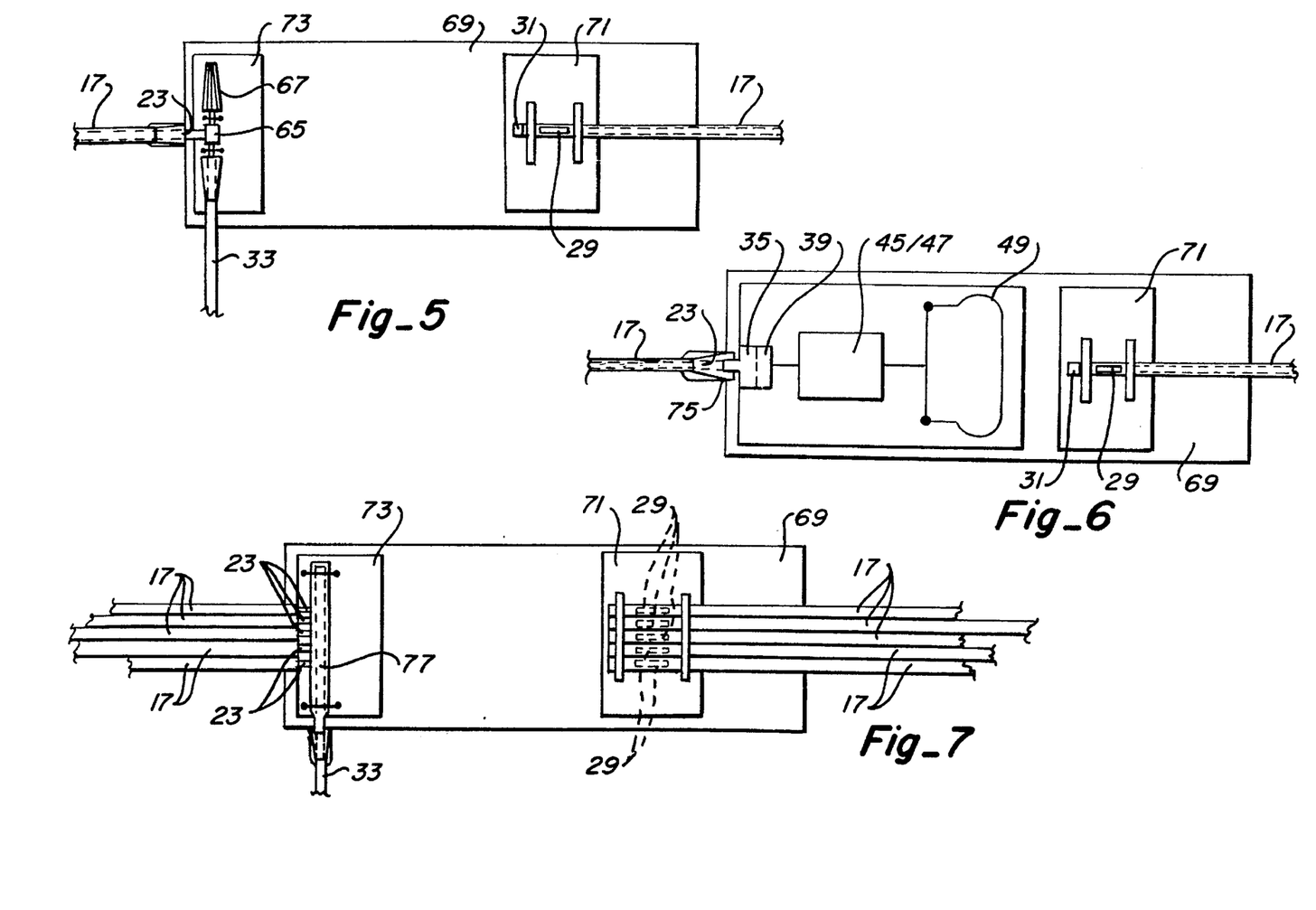
FIG. 5 is an illustration of one means for maintaining the detector of this invention on the body of a user.
FIG. 6 is an illustration of a preferred arrangement of the monitor of this invention which is worn by a user.
FIG. 7 is an illustration of a second embodiment of the breath detector of this invention.

FIGS. 1A and 1B illustrate monitor 15, including breath detector 17, of this invention. Monitor 15 includes breath detector 17 attached around the torso of the user and associated monitoring circuitry 19. Associated circuitry 19 is preferably battery powered, and may be independently housed for attachment to the subject (for example, by clipping on a belt or wearing in a pocket) or in a free standing configuration (as might be used, for example, in a hospital or other care setting), or may be incorporated with detector 17 into a single, belt like structural unit as illustrated in FIG. 6.

Figure 10:
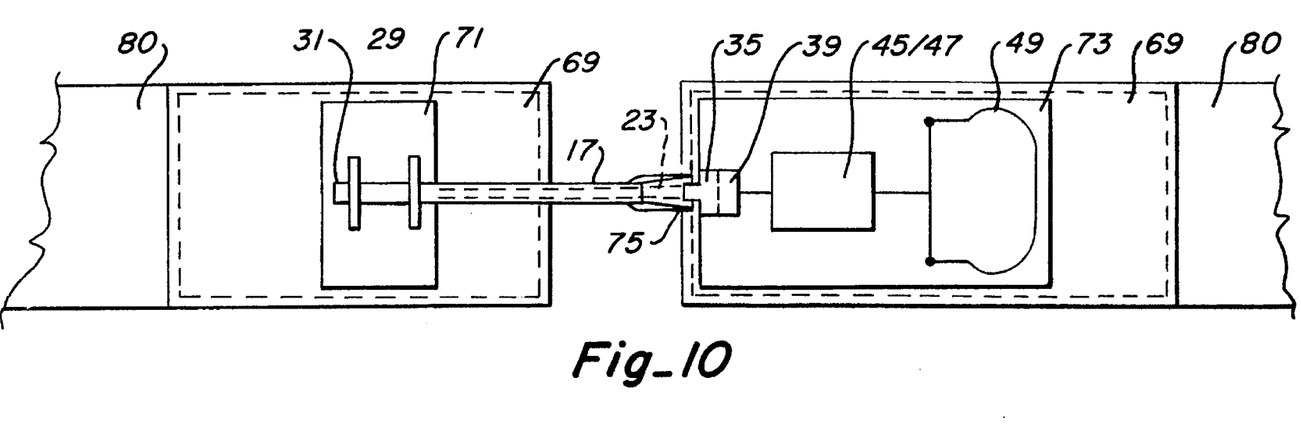
FIG. 10 is an illustration of a third embodiment of the breath detector of this invention.
Figure 11:
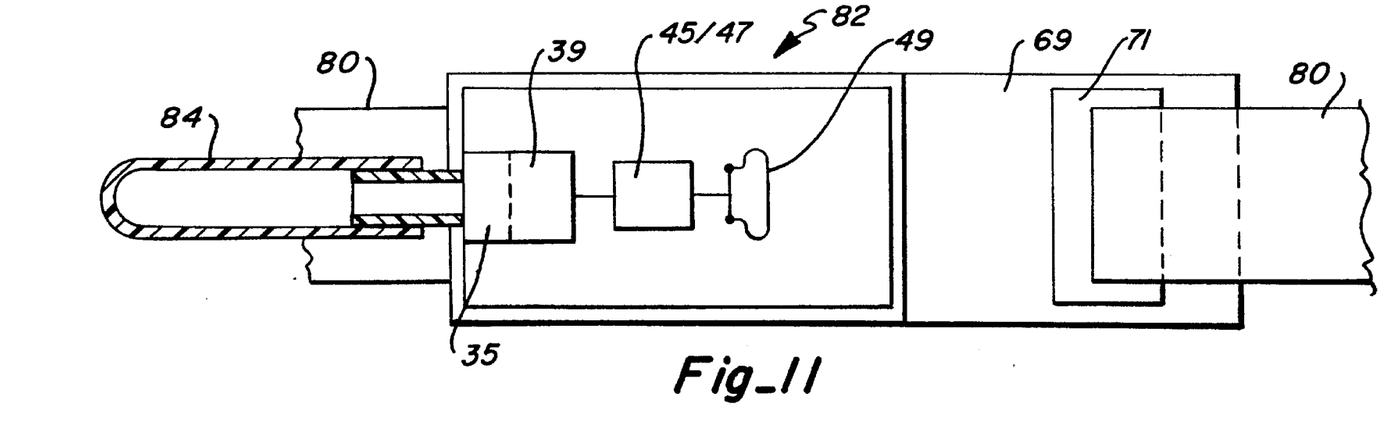
FIG. 11 is an illustration of a fourth embodiment of the breath detector of this invention.

Detector 17 is formed from a length of flexible yet resilient tubing (any length, depending on desired responsiveness desired by the particular application, may be employed from a length sufficient to wrap entirely around the subject as shown in FIG. 1 to very short lengths as shown in FIGS. 10 and 11), such as 602–305 Silastic (a trademark of Dow Corning Corporation) medical grade tubing, which, due to the relationship of material durometer, wall thickness and/or tube diameter, automatically regains its shape (both in terms of length and cross-sectional shape) after subjection to any mechanical deforming force such as stretching, flattening, kinking or the like.

In one embodiment, the tubing has a circular cross section (though an elliptical or other curvilinear cross section would also be effective), with a 0.078" inside diameter and a 0.125" outside diameter. The tubing is preferably made of silicon or similar material having a durometer of about Shore A54 and a wall 21 (FIG. 2) thickness of about 0.047", though any wall thickness and material could be utilized which exhibits the desired characteristics. It should be understood that the material utilized must not be so stiff or rigid that it will not yield to forces tending to change its geometry, nor so soft or flexible that the tube will not regain its shape after deformation and/or be easily kinked. Wall thickness will be related to external noise entering into the system.

The simplified structure of detector 17 presents a clear advantage over prior art devices which require substantial additional structure, such as a foam rubber insert, to assure that the fluid cavity will regain its undeformed geometry (see U.S. Pat. Nos. 4,602,643 and 4,813,428). Furthermore, the small diameter tubing greatly reduces pressure, or air movement, exerted at the pressure sensor (as hereinafter set forth) thus overcoming the need for specialized housings, barrier structures, secondary pressure chambers and the like which might be necessary where greater pressure and/or volumes of air are being exerted at the sensor. The foregoing greatly simplifies manufacture and reduces the likelihood of component failure while providing a reliable output indicative of subject respiration, and, in some embodiments, a more readily differentiatable output from the monitor.

Figure 3:
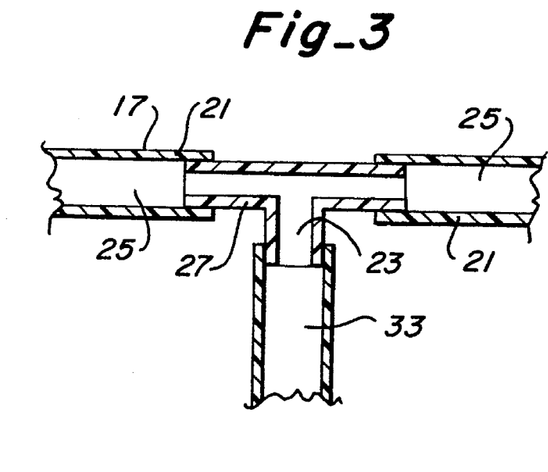
FIG. 3 is a sectional view of one arrangement for interconnection of the detector and transducer of FIGS. 1 and 2.

Tube 17 can be of any length (see, for example, FIG. 10), but in its simplest form, as shown in FIG. 1, is of a length sufficient to circle the entire torso of the subject (either inside or outside of the subject's clothing). The tube is configured so that but a single outlet 23 from channel, or conduit, 25 is provided. This may be accomplished utilizing tee junction 27 (as shown in FIGS. 1A and 3) having three access openings, plugs 29 in end or ends 31 (as shown in FIGS. 5, 6 and 7), or in any other manner consistent with the goal of creating a fixed internal volume of the tube or tubes having a single outlet.

Small diameter flexible tube 17 thus contains a fixed volume of fluid (preferably air), with the volume of channel 25 of tube 17 being altered by the breathing of the subject thereby causing low frequency pressure variations at outlet (or outlets) 23. Using, for example, Silastic tubing from Dow Corning Corporation, when the flexible tubing is placed snugly on the subject it will stretch (lengthen) during inhaling. While this stretching tends also to diminish tube diameter (at least along some of its length), since the tube length increases more than the diameter decreases, overall tube volume increases thus lowering fluid pressure in the tube. When exhaling occurs, the resiliency of the material causes the tube to return to its original shape (or, in the case of more complete evacuation of the lungs, to a shape approaching its shape when not snugly secured around the subject), thereby decreasing tube volume and increasing fluid pressure in the tube.

Figure 2:
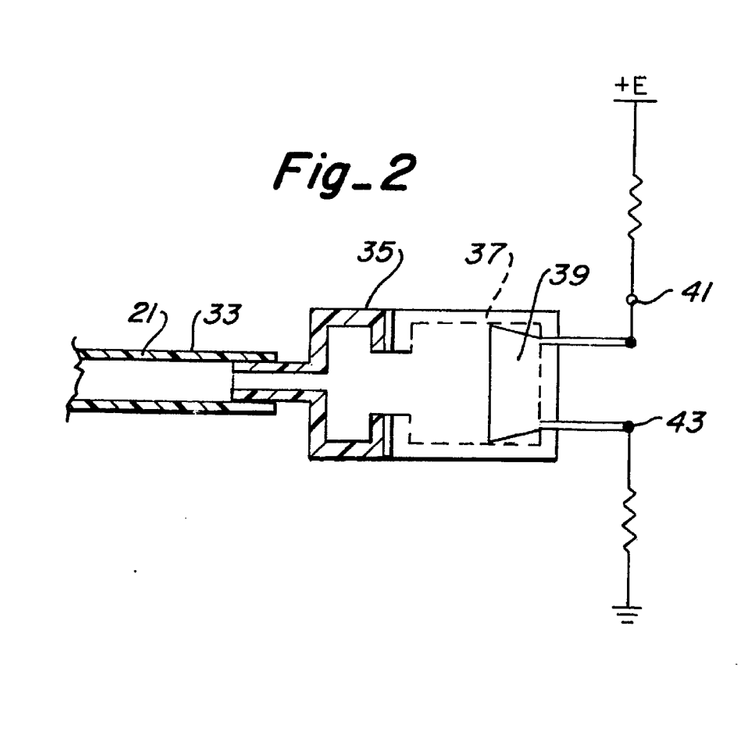
FIG. 2 is a schematic illustration of the transducer assembly Of the monitor of FIG. 1.

In the embodiment of the invention illustrated in FIGS. 1 and 2, interconnecting tube 33 (of any length suitable for its intended reach) is utilized to connect detector 17, at outlet 23, to pressure transducer manifold 35 connected (for example by a sealing adhesive) with transducer housing 37 having pressure transducer 39 of circuitry 19 therein.

Transducer 39 can be any type of pressure transducer. However, an electret capacitor microphone has been found to be preferable, providing a signal with good signal to noise ratio at its output 41 or 43. Electret microphone transducer 39 is mounted in housing 37 without need of any isolating film or the like utilized in other devices (see U.S. Pat. No. 4,813,428) to prevent over pressurization at the location of transducer 39 and/or saturation of the output. This is so because, unlike prior art devices utilizing larger pneumatic sensing cavities, tube 17 creates only relatively small changes in pressure at outlet 23 responsive to respiration or other movement.

The output signal from transducer 39, indicative of a subject's breathing patterns, is input to active low pass filter 45 having a center frequency of about 2 Hz and approximately 24 DB/octave attenuation. Filter circuit 45 (as more fully described with reference to FIG. 4) reduces artifact in the signal due to subject movement and/or non-breathing related impacts on detector 17. The output signal from filter 45 may be used to modulate transmitter 47 (operating at any selected frequency and being either AM or FM modulated) the output of which is applied at antenna 49 for broadcast to receiver/monitor unit 51 at another location (with the signal output therefrom preferably including a DC signal component such that upper airway obstruction, yawns, and fast or slow breathing may be further analyzed).

Figure 4:
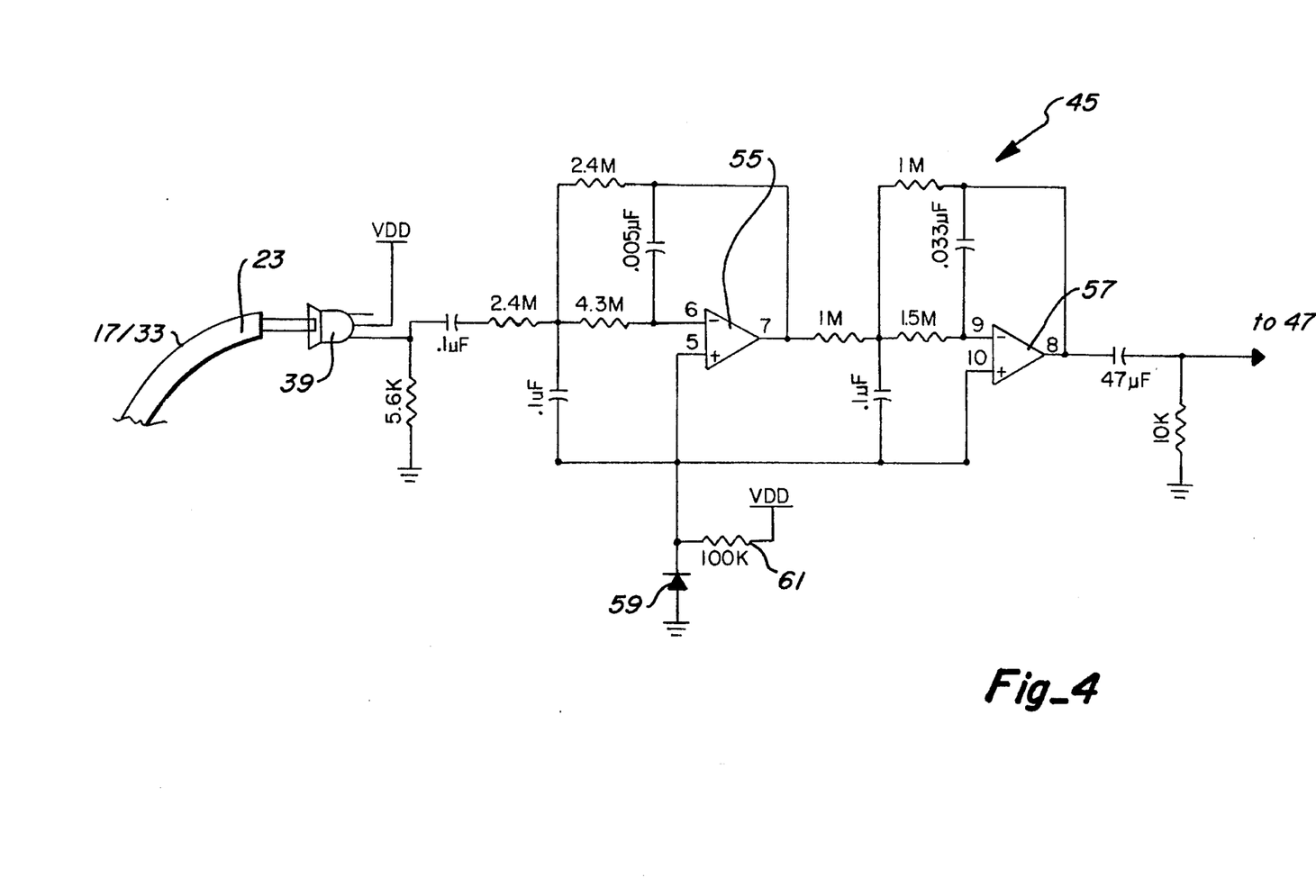
FIG. 4 is a schematic illustration of the transducer and low pass filter of the monitor of this invention.

Turning now to FIG. 4, low pass filter 45 is illustrated. Filter 45 has a cut-off frequency of between about 0.5 and 3 Hz (the lower end providing the best result in terms of movement artifact reduction in the signal but also reducing the upper limit of the detected respiration frequency), and preferably a cut-off at about 2.2 Hz. The embodiment of filter 45 illustrated is an active, four pole low pass configuration (known as an infinite gain, multiple feedback low pass filter with a Butterworth response). This configuration minimizes the frequency response changes due to component tolerance.

Resistor 61 and diode 59 are used to bias amplifiers 55 and 57 (for example, Linear Technology LT1179 operational amplifiers). Since this infinite gain, multiple feedback configuration is an inverting one, amplifiers 55 and 57 together provide an output that is in phase with the input from the subject (i.e., a positive going signal is output responsive to the subject's inhaling). Transducer 39 (herein a Digi-Key P9932 or equivalent) provides an increased current at its output responsive to increased fluid pressure at its input. Utilizing the material above described for tube/detector 17, wherein the volume of the tube increases due to tube deformation caused by inhaling, when the subject inhales a decreased fluid pressure results in the tube, thereby providing a negative going output voltage. Since this signal is inverted by filter circuit 45, a positive output voltage is output from filter circuit 45, thus being in phase with the input, a breath taken by the subject. Upon exhaling, the reverse is true (i.e., a negative output voltage from filter circuit 45 occurs).

Figure 8:
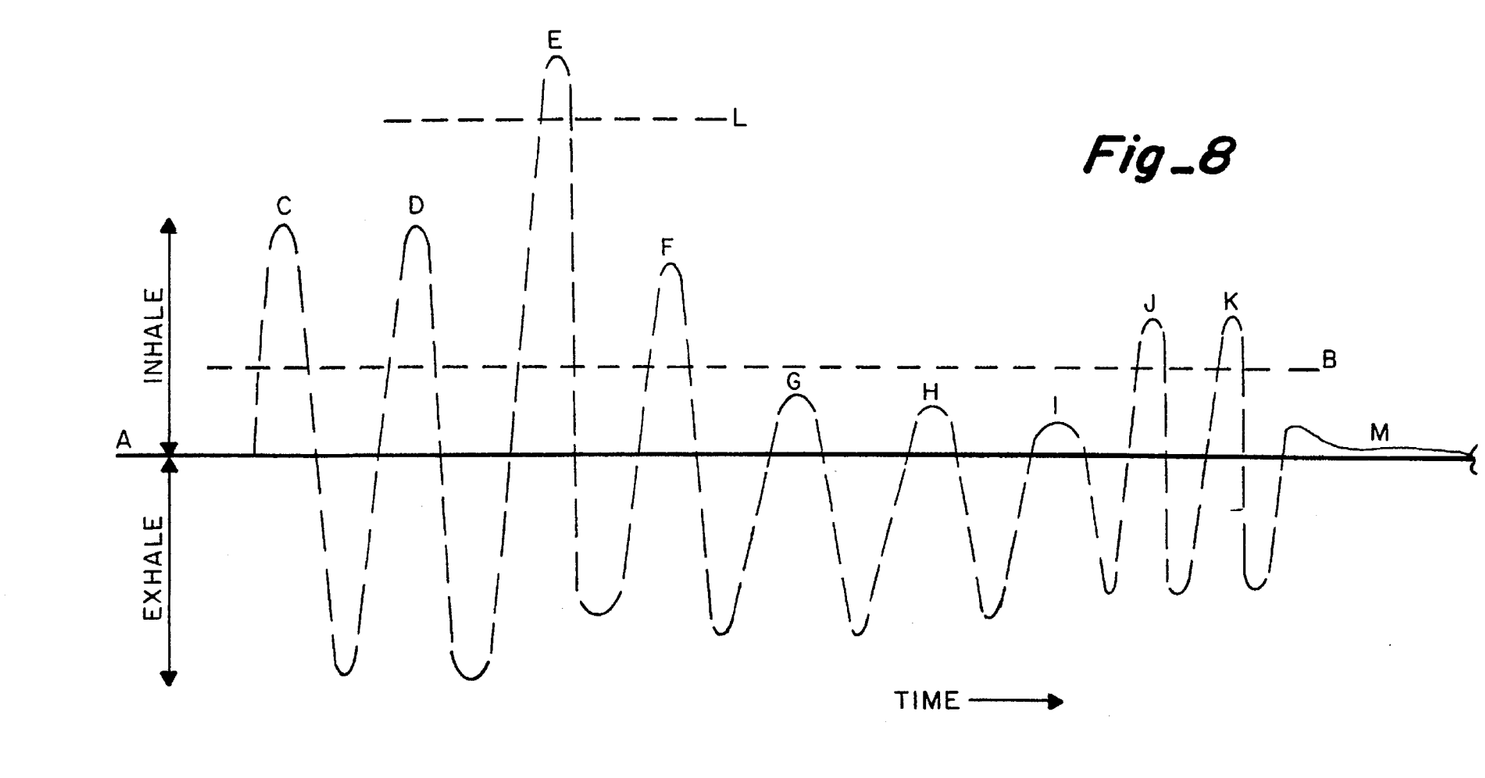
FIG. 8 is an illustration of exemplary waveforms output from the respiration monitor of this invention.

FIG. 8 illustrates the output signal waveform from filter 45 (or transmitter 47) with line A indicating the reference level below which exhaling is indicated and above which inhaling is indicated. The level indicated by line B is established (by appropriate processing at receiver 51 or internally with circuitry 19) as a breath detection threshold, with signals exceeding the threshold being interpreted as a breath. Signals, including noise, which do not achieve threshold B are interpreted as no breath. Thus, pulses C, D, F, J and K indicate normal breathing, though of different rates. Pulse E exceeds a second threshold L (again established in software, where desired) which indicates a sigh or yawn.

Obstructive apnea is indicated by pulses G, H and I because threshold B is not reached and the amplitude below reference level A exceeds the amplitude of the waveform above level A (of course the reverse situation could also be true, software being configured to accommodate either occurrence). Waveforms J and K, by virtue of slightly decreased amplitude but increased frequency, indicate more rapid, shallow breathing. As the waveform at M approaches level A, a cessation of breathing is indicated.

The output waveform can be monitored in a variety of ways which are known to those skilled in the art (utilizing different references and thresholds, counting the inhale and exhale pulses and the like) so that irregular breathing problems can be sensed and differentiated from the received waveform. The amplitude of the signal above reference A will be proportional to the volume of air drawn into the lungs and the amplitude of the signal below reference A will be proportional to the volume of air and $CO_2$ expelled from the lungs. As may be appreciated, utilizing the above described system, those monitoring the subject's breathing are better able to distinguish various breathing patterns and events (such as obstructive apnea, breath holding, yawning and the like) from one another.

Means of securing detector 17 around a subject is illustrated in FIG. 5. In this arrangement, one end 31 of tube 17 is plugged utilizing any suitable, preferably flexible, material 29, and tee 65 is modified by plugging access 67. A Velcro (or similar material) loop pad 69 of a selected length is provided for variably positionable receipt of Velcro hook pads 71 and 73. Pad 71 has end 31 of detector 17 secured thereto at each side of plug 29 (for example, using stainless steel staples), and pad 73 has tee 65 affixed thereto (for example, by stitching or the like). In this manner, the detector can be positioned around the subject sufficiently snugly to achieve volume deformation during breathing, and can accommodate subjects of differing girth.

FIG. 6 shows the preferred arrangement of the monitor, all of which, including detector 17, transducer 39, filter 45, transmitter 47 and antenna 49, are incorporated into a wearable unit. As previously shown in FIG. 5, a Velcro loop pad 69 and hook pad 71 are provided. However, transducer 39, filter 45, transmitter 47 and antenna 49 are mounted modularly to pad 69 (for example using a fabric substrate and a conformal coating or the like, with a protective cover) using an adhesive or other suitable means for attachment. Manifold 35 is then utilized to receive directly end 75 (outlet 23 from channel 25) of detector/tube 17, thus providing a compact wearable monitor.

An alternative embodiment of the breath detector of this invention, utilizable with any of the arrangements illustrated in FIGS. 1, 5 or 6, is shown in FIG. 7. Multiple tubes 17 are arranged for application around the subject, the tubes each having a single outlet joined at manifold 77 to again provide a single known volume or capacity. Use of multiple tubes will increase detector sensitivity and improve artifact rejection of the overall system.

Figure 9:
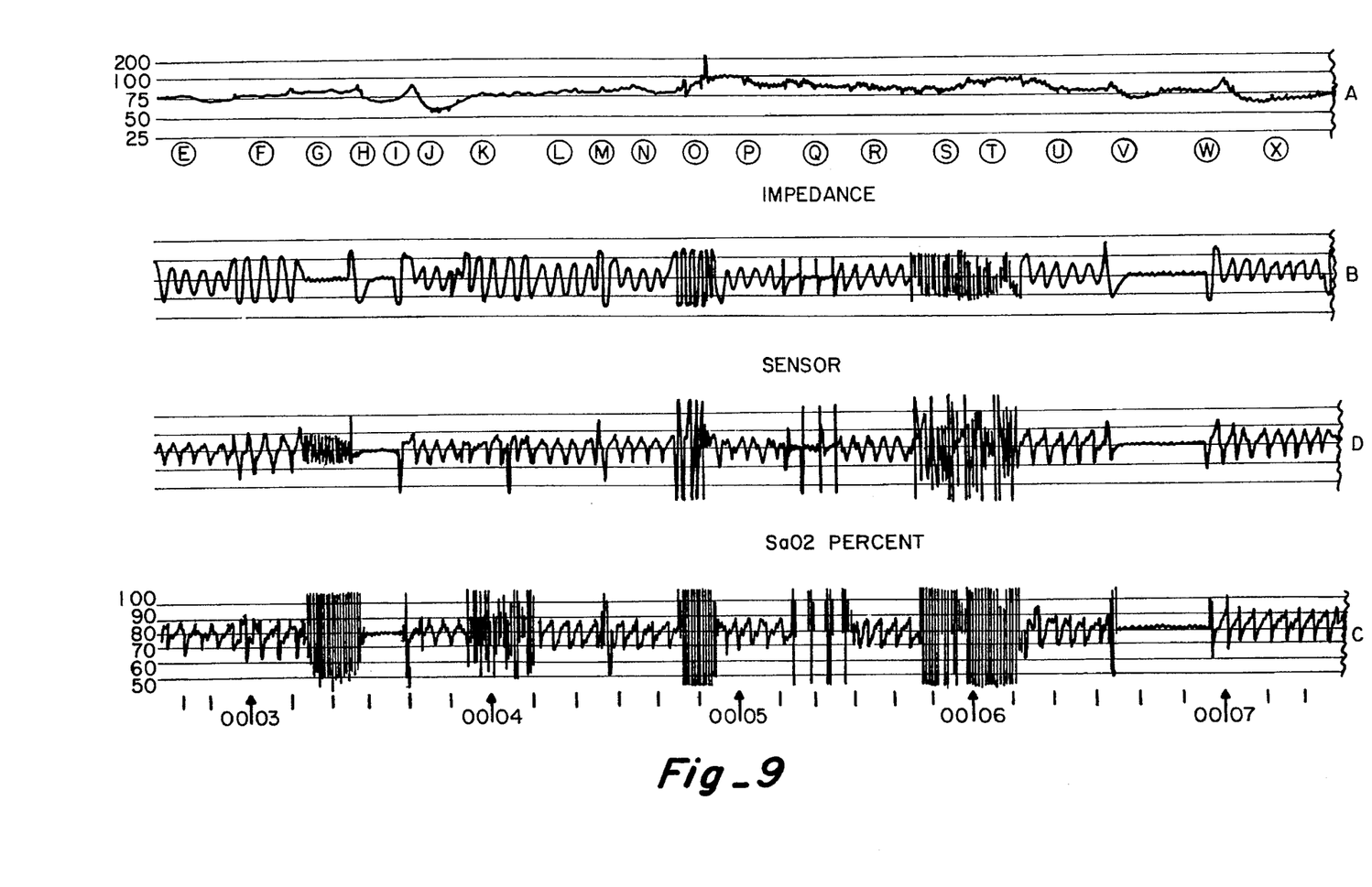
FIG. 9 is a chart illustrating actual waveforms of the monitor of this invention (both filtered and unfiltered) compared with the output of a prior art pneumographic monitor.

FIG. 9 shows data comparing waveforms for average heart rate of a subject (A), a prior art impedance pneumographic monitor (B), the unfiltered output from transducer circuitry 39 of the monitor of this invention (C), and the filtered output from monitor 15 of this invention (D). Regular breathing is shown at E, J, L, N, P, R, U and X, and deep breathing is shown at F. Holding of breath (cessation of breathing) is shown at H and V. Of particular note, however, is the ability of monitor 15 to more clearly distinguish fast shallow breathing (G) from cessation of breathing (H and V). Also note that the output of monitor 15 goes positive and then level at H and V while the prior art monitor goes positive and then negative before the held breath (of key importance in differentiating obstructive apnea). I and W indicate release of the held breath.

The application of monitor 15 to distinguish and monitor obstructive apnea is further illustrated at Q (slow obstructive apnea) and S (fast obstructive apnea). Because the output waveform is in phase with the actual respiratory event, unlike the prior art unit, three distinct episodes of chest cavity fluctuation (the waveform first goes in a negative direction, then in a positive direction) are detected (unlike the prior art device which first goes positive with the negative transition, quite similar to holding ones breath). By counting the pulses, the care giver can determine the number of times the chest cavity has fluctuated during obstructive apnea.

At K, normal breathing while shaking tube 33 is illustrated. The movement artifact is quite pronounced in the unfiltered output (C) of monitor 15, while the filtered output (D) clearly shows the effectiveness of filter 45 in removing signal not indicative of breathing (the filtered output indicating normal breathing).

At M, the occurrence of a sigh is more clearly registered by monitor 15. At O and T (occurrences of coughing and crying, respectively), while both signals B and D indicate that something unusual is occurring, because of the use of electret transducer microphone 39 in the configuration of monitor 15 as set forth herein, the signal from monitor 15 may be linked to an amplifier and speaker (or earphones) and the actual sound of coughing or crying of the subject will be heard (which is not the case with the prior art device).

FIG. 10 illustrates the detector of this invention wherein tube 17 is substantially shortened (as before, however, function is the same). Loop pads 69 are attached (for example, by sewing) at opposite ends of belt 80 for receipt of the detector/monitor system snugly adjacent to the subject's torso when belt 80 is applied therearound.

Yet another embodiment 82 of this invention is illustrated in FIG. 11. Herein, rather than tube 17 being utilized, a flexible yet resilient bulb 84 connected to manifold 35 is utilized to detect breathing. As bulb 84 (akin to an eye dropper bulb) is flexed due to inhaling and returns to its initial shape during exhaling, fluid pressure changes within the bulb are sensed at transducer 39. It should be noted, however, that during inhaling, the volume of bulb 84 is reduced due to bulb deformation, while volume is increased during exhaling when bulb 84 returns to its original shape. Thus, an increase in output voltage from transducer 39 is indicative of inhaling (increased fluid pressure results at transducer 39 due to decreased volume). A variety of alternative designs, such as bellows type structures, could be utilized for the breath detector of embodiment 82.

As may be appreciated, an improved respiration monitor including a simplified, yet reliable, breath detector is provided for application in a variety of settings, including infant monitoring, personal emergency response systems, athletic training, human or animal care units, personal security systems and the like.

What is claimed is:

1. A breath detector for connection with monitoring means including pressure sensing means for monitoring changes in capacity of said detector, said detector comprising:

at least a first hollow tube having a fluid channel defined between first and second ends of said tube, said fluid channel normally having a substantially constant diameter from said first end to said second end and providing said capacity, said tube having an outlet from said channel and having flexibility sufficient to respond, by deformation of said tube, to breathing of a subject when secured adjacent to the subject's torso and resiliency sufficient to regain its original shape after deformation without other structural aid;

securing means for securing said tube adjacent to the subject's torso; and connecting means for connecting said outlet of said tube with the pressure sensing means of the monitoring means.

2. The detector of claim 1 wherein said tube is stretchable so that overall volume of said channel increases when a subject having said tube applied adjacent to the subject's torso inhales.

3. The detector of claim 1 wherein said flexibility of said tube is insufficient to totally close said channel when said tube is exposed to a variety of external pressures.

4. The detector of claim 1 further comprising at least one additional flexible yet resilient hollow tube having an outlet for a fluid channel defined thereby, and wherein said connecting means includes manifold means for connecting said outlets of said tubes with the monitoring means.

5. The detector of claim 1 wherein said securing means is at said first and second ends of said tube.

6. The detector of claim 1 wherein said tube has a second outlet, said securing means comprising a junction having at least first, second and third access openings, said first access opening providing said connecting means, said outlets of said tube secured to different ones of said second and third access openings of said junction.

7. A respiration monitor comprising:

a respiration detector including stretchable means defining a hollow conduit having a volume for containing a quantity of fluid and an outlet, said conduit having a substantially constant diameter between ends of said stretchable means when said stretchable means is in an unstretched condition, said stretchable means configured so that when stretched said volume of said conduit increases;

means for applying said respiration detector adjacent to the subject's torso in a manner allowing stretching of said stretchable means responsive to inhalation by the subject; and pressure sensing means connectable at said outlet of said stretchable means of said detector for sensing pressure changes at said respiration detector due at least in part to said stretching and having as an output therefrom an electrical signal which is variable with sensed pressure.

8. The monitor of claim 7 further comprising low pass filter means for receiving said signal from said pressure sensing means and reducing artifact in said signal not related to respiration of a subject, said low pass filter means providing an output therefrom indicative of the subject's respiration.

9. The monitor of claim 8 further comprising transmitting means for receiving said output from said low pass filter means, said transmitting means including an antenna for transmitting a signal indicative of said received output from said low pass filter means.

10. The monitor of claim 7 wherein said low pass filter means is configured to provide said output therefrom in phase with the subject's breathing and has a cutoff between about 2.0 and 2.5 Hz.

11. The respiration monitor of claim 7 wherein said pressure sensing means is an electret microphone transducer.

12. The monitor of claim 11 wherein said electret microphone transducer is exposed to pressure changes exerted from said conduit without intervening structure.

13. The monitor of claim 7 wherein said detector comprises a flexible yet resilient hollow tube of one-piece construction and having said fluid conduit substantially entirely defined by a wall of said tube.

14. A respiration monitor comprising;

a breath detector including stretchable means defining a hollow conduit having a volume for containing a quantity of fluid and an outlet, said conduit having a substantially constant diameter between ends of said stretchable means when said stretchable means is in an unstretched condition, said stretchable means configured so that when stretched said volume of said conduit increases;

means for applying said breath detector adjacent to the subject's torso in a manner allowing stretching of said stretchable means responsive to inhalation by the subject;

a pressure transducer connected with said detector for sensing indications of volumetric changes in said detector and providing an electrical signal output indicative thereof; and an active low pass filter utilizing feedback, said low pass filter receiving said output from said transducer and providing an output indicative of the subject's respiration, said filter having a cutoff no greater than about 3 Hz.

15. The monitor of claim 14 wherein said pressure transducer is an electret microphone.

16. The monitor of claim 14 wherein said cutoff of said low pass filter is between about 0.5 and 2.5 Hz.

17. The monitor of claim 14 further comprising transmitting means for receiving said output from said low pass filter, said transmitting means including an antenna for transmitting a signal indicative of said received output from said low pass filter.

18. The monitor of claim 17 wherein said means for applying said breath detector adjacent to the subject's torso is configured for mounting of said transducer, said low pass filter and said transmitting means thereto.

* * * * *